(12) United States Patent
Pauker et al.

(10) Patent No.: US 7,889,434 B2
(45) Date of Patent: Feb. 15, 2011

(54) ZOOM LENS FOR ENDOSCOPIC DEVICES

(75) Inventors: Fritz Pauker, Kissing (DE); Thomas Viehbach, Diepoltshofen (DE); Konstantin Bob, Weinheim (DE)

(73) Assignee: STM Medizintechnik Starnberg GmbH (DE)

(*) Notice: Subject to any disclaimer, the term of this patent is extended or adjusted under 35 U.S.C. 154(b) by 1540 days.

(21) Appl. No.: 11/136,818

(22) Filed: May 25, 2005

(65) Prior Publication Data

US 2005/0270664 A1 Dec. 8, 2005

(30) Foreign Application Priority Data

May 27, 2004 (DE) .................. 10 2004 026 005

(51) Int. Cl.
*G02B 1/06* (2006.01)
*A61B 1/055* (2006.01)

(52) U.S. Cl. ............... 359/666; 359/676; 600/174; 600/167

(58) Field of Classification Search ........... 600/167, 600/173, 174, 176, 168; 359/362, 365, 380, 359/665–667, 694, 823, 379, 703, 704, 676–690
See application file for complete search history.

(56) References Cited

U.S. PATENT DOCUMENTS

| | | | |
|---|---|---|---|
| 3,161,718 A | 12/1964 | De Luca et al. | |
| 4,286,839 A | 9/1981 | Ilzig et al. | |
| 4,331,388 A | 5/1982 | McCrobie et al. | |
| 4,805,598 A * | 2/1989 | Ueda | 600/176 |
| 5,406,417 A | 4/1995 | Denvenyi | |
| 5,440,431 A * | 8/1995 | Jeong | 359/704 |
| 5,684,637 A * | 11/1997 | Floyd | 359/666 |
| 7,230,771 B2 * | 6/2007 | Kuiper et al. | 359/665 |
| 2008/0030872 A1 * | 2/2008 | Nishioka et al. | 359/683 |

FOREIGN PATENT DOCUMENTS

| | | |
|---|---|---|
| DE | 19733628 A1 | 7/1997 |
| DE | 19710668 | 9/1998 |
| DE | 19710688 A1 | 9/1998 |
| EP | 1705507 | 9/2006 |
| FR | 2634287 | 1/1990 |
| JP | 55052009 | 10/1978 |
| JP | 2000249813 | 9/2000 |
| WO | WO 97/36193 | 10/1997 |

OTHER PUBLICATIONS

European Patent Office Search Report.
European Search Report, issued by the European Patent Office in connection with European application No. EP05001729, 1 page.

* cited by examiner

*Primary Examiner*—John P Leubecker
*Assistant Examiner*—Victoria W Chen
(74) *Attorney, Agent, or Firm*—Hanley, Flight & Zimmerman, LLC

(57) ABSTRACT

A zoom lens for use in endoscopic devices, in which a plurality of lens units is arranged in a lens cylinder perpendicular to the center line thereof. Among the plurality of lens units at least one lens unit may be hydraulically adjustable in the axial direction of the lens cylinder so as to vary the focal length of the zoom lens. Furthermore, the focal length of individual lenses of the lens unit may be varied by pneumatically varying the shape of the lenses in order to vary the total focal length of the zoom lens in this way.

25 Claims, 9 Drawing Sheets

ZOOM LENS FOR ENDOSCOPIC DEVICES

BACKGROUND OF INVENTION

1. Field of the Invention

The invention relates to a zoom lens for use, for instance, in endoscopes and/or endoscopic devices.

2. Discussion of the Prior Art

Endoscopes have become an important aid in the fields of engineering and medicine in order to inspect duct-shaped hollows or cavities which otherwise are accessible by considerable operations only. At their leading end endoscopes are equipped with a lighting means and with an optical system for visually detecting the area in the front of the hollow. The optical information detected at the leading end of the endoscope is normally either transmitted through the endoscope backward to its operating end by means of fiber optics, or it is detected by means of an optical sensor chip at the leading end, is transmitted via an electric wire through the endoscope and is made visible on a screen. Moreover a radio transmission of the information detected at the leading end of the endoscope to the operating end is possible.

The patent application DE 102 54 609.6 which is not yet published describes an endoscope head equipped with a number of functional units, such as e.g. an optical system, lighting elements, rinsing nozzles and the like. The optical system of the endoscope head substantially consists of a cubical sensor chip chamber, a cylindrical lens chamber lying there above and being separated from the sensor or camera chip chamber by a partition, which lens chamber receives at least one optical lens and/or a lens system directly fixed in the lens chamber or adapted to be inserted into the chamber in the form of a prefabricated cartridge. Although in DE 102 54 609.6 it is referred to the fact that the lens system can also be capable of being zoomed, no greater details, are described, however. Furthermore no information is provided about how such a lens system capable of being zoomed can be realized.

Due to the progress made in digital photography and the related graphical further processing of visual information, it is possible to magnify an obtained image or sections thereof by image processing programs. Thus by the aforementioned DE 102 54 609.6 an endoscope capable of zooming could be realized, to be sure, this technology includes the following drawbacks, however.

In image magnification by means of fixed lenses and subsequent further treatment (digital zoom) only a section of the image is enlarged, i.e. the number of pixels of which the image is composed remains the same. In other words, the resolution of the image is deteriorated and the sharpness as well as the image quality of the magnified section get worse. Also in this case good image processing programs offer the function of maintaining the original resolution by means of interpolation, however the image information which is mathematically added is no real visual information but these are statistically calculated pixels. Thus, although details can simulate sharpness, they can be falsified in reality.

Hence when enlarging image sections, there is only the possibility of an optical zooming so as to obtain a sharp and true-to-detail image. In endoscopes, however, due to the miniaturized design the problem arises that the technologies conventionally used in photography, such as e.g. a piezoelectric adjustment of the lenses, is not applicable for varying the focal length, because they require by far too much space which is not provided in an endoscope head.

In order to solve the above-stated problems it is an object of the invention to realize a zoom lens for use in an endoscope which permits sufficient resolution in a small construction space.

SUMMARY OF THE INVENTION

The foregoing object of the invention is achieved by a zoom lens comprising a lens mount, a plurality of lens units, at least one lens unit of which is hydraulically/pneumatically adjustable, and is arranged in a lens mount substantially perpendicular to the center line thereof. The lens mount, for instance, may be a cylinder which is preferably formed integrally with an endoscope head or is inserted in the same.

Between respective neighboring lens units advantageously a fluid chamber is formed to which optionally fluid conduits are connected. The hydraulic adjustment of the at least one lens unit in the axial direction of the lens cylinder for varying the focal length of the zoom lens is effected by the fact that preferably incompressible fluid is supplied to the respective fluid chambers and/or discharged from the respective fluid chambers.

Individual lenses of a lens unit can form hollows or cavities. The focal lengths of the individual lenses and thus the total focal length of the zoom lens can be adjusted by varying the difference in pressure between the respective hollows of the lenses and the ambience or surroundings of the lenses.

One substantial advantage of a hydraulic/pneumatic adjustment of the lens units is the small space required in the direct ambience or immediate area surrounding the zoom lens in the endoscope head. Previous zoom lenses have required a large space in the direct ambience of the lenses for arranging the lens drive. The advantage of the hydraulic/pneumatic adjustment resides in the fact that the motor operator need not be arranged in the ambience of the lenses but may be displaced to a position where the space required is of minor importance. The fluid conduits required for such an adjustment are embedded in the endoscope shaft in which more space is available compared to the endoscope head.

Further advantageous configurations of the invention are the subject matter of the claims.

BRIEF DESCRIPTION OF THE DRAWINGS

Hereinafter the invention is described in detail by way of preferred embodiments with respect to the enclosed drawings, where the following is schematically shown in the drawings.

DETAILED DESCRIPTION OF THE PREFERRED EMBODIMENTS

An endoscope (not shown) substantially consists of a flexible endoscope shaft (not shown) to the leading end of which an endoscope head (not shown) is attached and to the other end (operating end) operating and information evaluating devices (not shown) are connected. This endoscope head can be equipped with various means and tools, such as for instance the zoom lens presented in this invention. The terms "leading/front" and "rear" used in the description refer to the direction of use of the endoscope; hence the leading end of the endoscope is the end which is introduced into the hollow, passage or cavity during use.

First Embodiment

Figure 1:
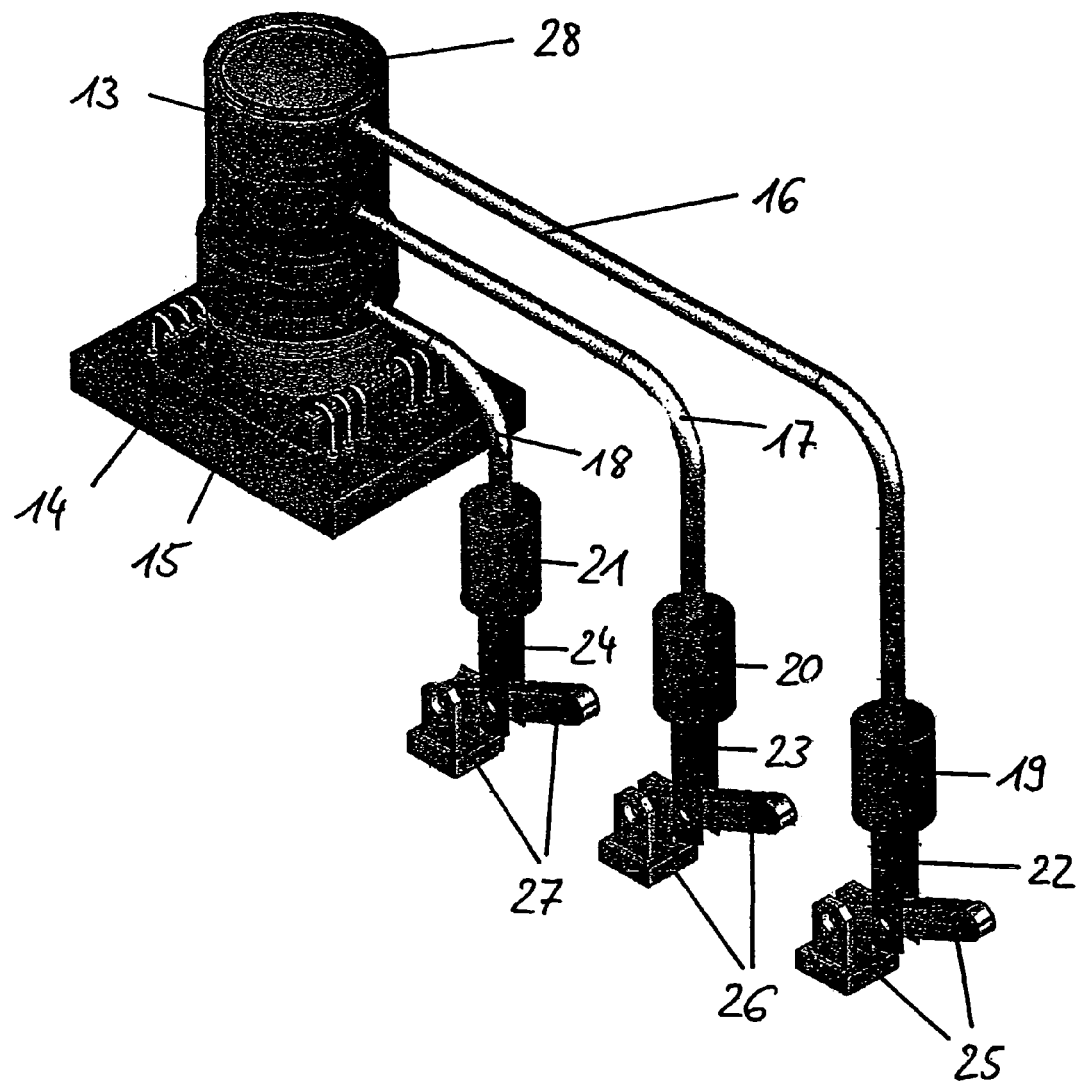
FIG. 1 is a spatial representation of a first embodiment of the zoom lens of the present invention.
Figure 2:
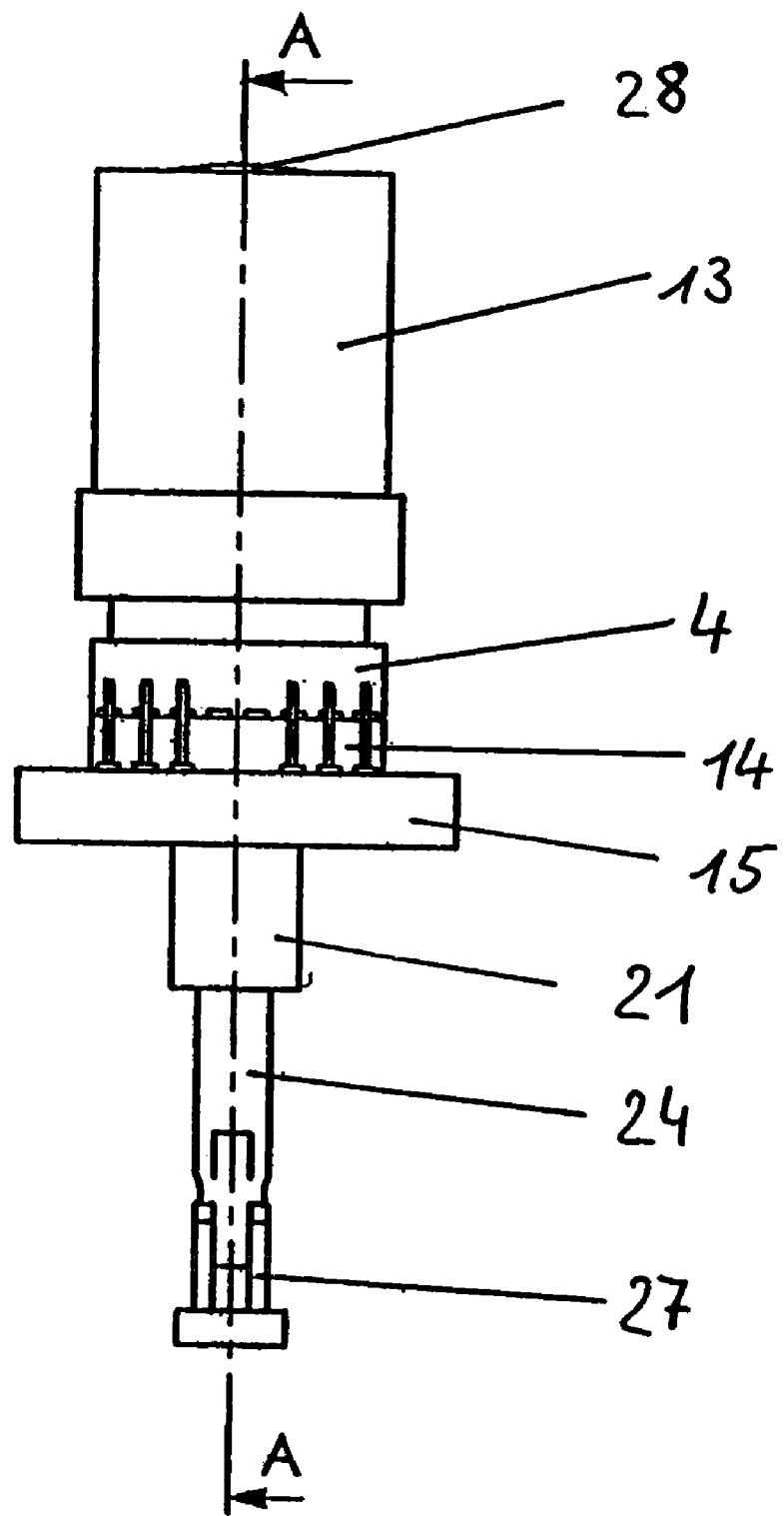
FIG. 2 is a side view of the zoom lens from FIG. 1.
Figure 3:
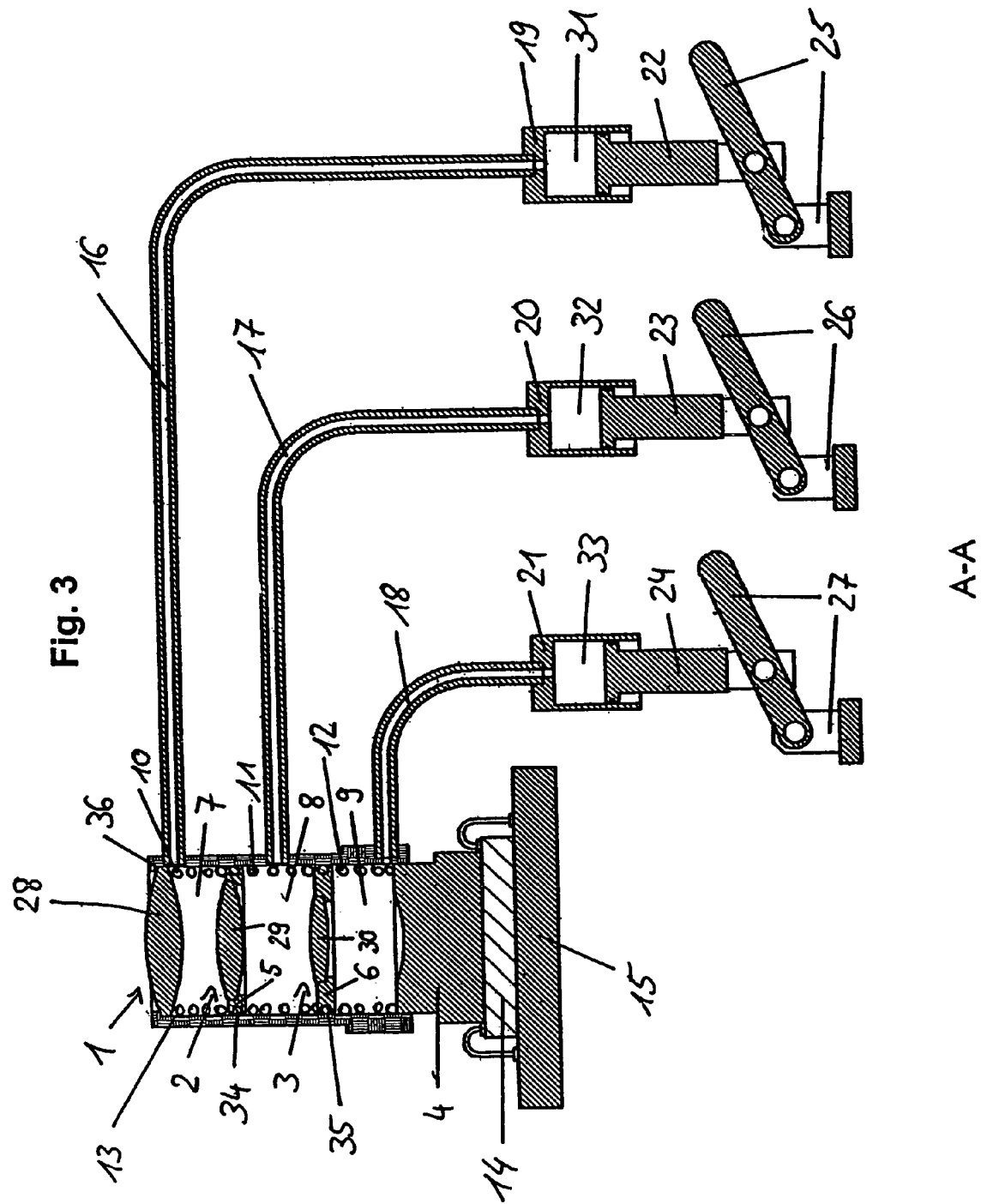
FIG. 3 is a sectional front view along the section A-A from FIG. 2.

By way of the FIGS. 1 to 3 the zoom lens for use in an endoscope head (not shown) according to a first embodiment is described in detail. The zoom lens consists of a substantially tubular lens cylinder 13 which is either integrally connected with an endoscope head (not shown) or is detachably mounted in the latter.

The lens cylinder 13 accommodates four lens units 1-4 in the present embodiment. The lens unit 1 comprises a lens 28 which is arranged at the leading end of the lens cylinder 13 in the same, perpendicular to the center line of the lens cylinder 13. The outer diameter of the lens 28 is appropriately adapted to the inner diameter of the lens cylinder 13 so that the lens cylinder 13 is closed to be fluid-tight to the front. At its leading end the lens cylinder 13 has a projection 36 which extends evenly from the inner surface of the lens cylinder 13 to the inside. Thus at the position of the projection 36 the inner diameter of lens cylinder 13 is larger than the outer diameter of the lens 28, whereby the latter is held in the lens cylinder 13. Alternatively, also a different possibility could be imagined, such as e.g. a force fit to prevent the lens 28 from being removed from the front opening of the lens cylinder 13.

The lens unit 2 and the lens unit 3 are substantially circular and each of them is arranged perpendicular to the center line of the lens cylinder 13. Each consists of a lens 29 and 30, a lens mount 5 and 6 as well as a sealing ring 34 and 35. The lens mounts 5 and 6 have an annular shape, wherein in the central circular openings thereof a lens 29 and 30, respectively, is arranged. In the circular opening of the lens mounts 5 and 6, a web is inserted with respect to the longitudinal direction of the lens cylinder 13 so that the respective inner diameter of the lens mounts 5 and 6 at the front side (at the top in FIG. 3) is substantially equal to the outer diameter of the respective lenses 29 and 30 and at the rear side it is minimally smaller than the outer diameter of the respective lenses 29 and 30. The lenses 29 and 30 can then be inserted into the respective lens mounts 5 and 6 from the front and are exactly positioned relative to the lens mounts 5 and 6, because they are adjacent to the webs. The lenses 29 and 30 can be held in the lens mount, for instance, by a force fit or by gluing. The outer diameters of the lens mounts 5 and 6 are minimally smaller than the inner diameter of the lens cylinder 13 so that the lens mounts 5 and 6 are movable in axial direction of the lens cylinder 13. In each of the peripheral outer surfaces of the lens mounts 5 and 6 annular grooves are shaped, which receive respective sealing rings 34 and 35. These sealing rings 34 and 35 seal between the peripheral outer surfaces of the corresponding lens mounts 5 and 6 and the inner surface of the lens cylinder 13 so that fluid-tight fluid chambers 7-9 are formed which hereinafter will be described in detail.

The rear opening of the lens cylinder is closed by another lens unit 4. This lens unit has on its front half the shape of a cylinder the longitudinal axis of which corresponds to the longitudinal axis of the lens cylinder 13. The outer diameter of this cylinder shape corresponds to the inner diameter of the lens cylinder 13. The cylindrical front side of the lens unit 4 is then inserted in the rear opening of the lens cylinder 13 so that the latter is closed in a fluid-tight manner. Moreover the lens unit 4 has at its front side a central concave trough by which the light incident at the leading end of the lens is diffracted and transmitted to an optical sensor chip 14. The rear half of the lens unit 4 has a cubical shape, wherein the side length thereof in the plane perpendicular to the longitudinal axis of the lens cylinder 13 is adapted to the size of the optical sensor chip 14.

This optical sensor chip 14 is arranged with its photosensitive side at the rear side of the lens unit 4 and converts visual information into electric signals. The optical sensor chip 14 is mounted on a functional element 15 at its side turned away from the lens cylinder.

Due to the fluid-tight arrangement of the four lens units 1-4 the three fluid chambers 7-9, each of which is delimited by two neighboring lens units 1-4 and the inner surface of the lens cylinder 13, are formed between the lens units 1-4.

Flexible fluid conduits 16-18, respectively, lead from the fluid chambers 7-9 through the endoscope shaft (not shown) rearwards to the operating end of the endoscope shaft. These fluid conduits 16-18 are advantageously arranged in the center of the endoscope shaft, if possible, so as to keep an influence on the pressure of the fluid provided therein as small as possible. More exactly speaking, this means that when inserting the endoscope shaft in a hollow having plural strong bends, the endoscope shaft is likewise strongly bent which may result in a contraction of the cross-section of the fluid conduits 16-18 provided in the endoscope shaft at the bent positions. This contraction of the cross-section results in a pressure variation of the fluid provided in the fluid conduits, wherein the pressure variations in the individual fluid conduits 16-18 may differ depending on whether the respective fluid conduit 16-18 is arranged in the endoscope shaft more toward the outside or the inside of the curvature. This impedes an accurate adjustment of the lens units which will be described in more detail later. This effect of contraction of the cross-section is more weakened the more centrally the fluid conduits are arranged in the endoscope shaft. In order to reduce this influence on the pressure, the fluid conduits 16-18 are advantageously arranged as centrally as possible in the endoscope shaft in the present embodiment.

In each fluid chamber 7-9 a spring 10-12 is inserted which is a spiral spring in the present embodiment and is arranged so that the longitudinal axis thereof coincides with the longitudinal axis of the lens cylinder 13. Expediently, the outer diameter of the springs 10-12 is minimally smaller than the inner diameters of the lens cylinder 13 so that the motions of the springs are not decelerated or blocked when they are compressed or expand. The ends of the respective springs 10-12 are supported at the lens units and form an annular bearing surface with the latter. These springs may be biased in a desired manner to position the adjustable lens units 2 and 3 in a home or constructional position. An assembly of the lens is simplified by the fact that the springs 10-12 space two neighboring lens units from each other so that the sensitive lenses cannot contact each other when fluid is not yet filled into the fluid chambers 7-9. Moreover the springs 10-12 bring about a uniform-axial movement by their uniform pressing against the lens units 2 and 3 in the plane perpendicular to the longitudinal axis of the lens cylinder 13 and thus during movement they prevent the lens units 2 and 3 from tilting or jamming in the lens cylinder 13. Further aspects of the functioning of the springs 10-12 will be discussed hereinafter.

At the operating end of each fluid conduit 16-18 a cylinder 19-21 is connected in which a piston 22-24 is inserted to slide therein. From the outer surface of the piston 22-24 facing the inner surface of the cylinder 19-21 and the inner surface of the cylinder 19-21 an actuator chamber 31-33 is delimited which is communicated with the fluid chamber 7-9 through the respective fluid conduit 16-17.

Each of the fluid chambers 7-9, of the fluid conduits 16-18 and of the actuator chambers 31-33 is filled with an as incompressible fluid as possible which must have appropriate optical properties to suitably diffract the light rays because it is provided between the lens units 1-4.

Figure 4:
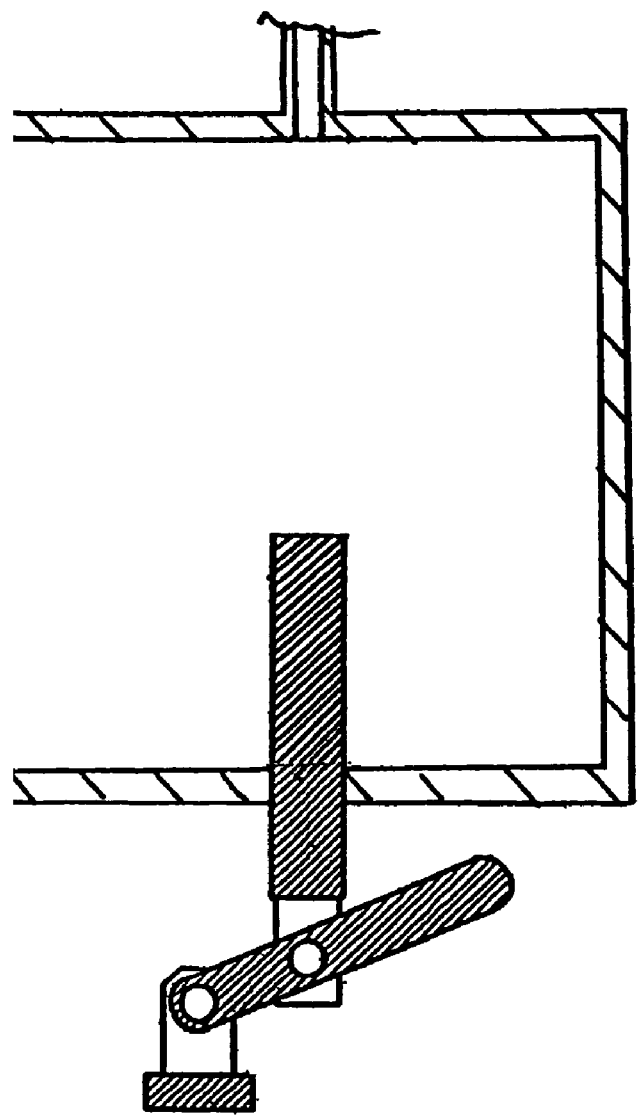
FIG. 4 shows a construction of a piston-cylinder unit according to a first embodiment.

Concerning the cylinder-piston-unit, it is advantageous when the outer diameter of the piston 22-24 is definitely smaller than the inner diameter of the cylinder 19-21, as shown in FIG. 4. In this way a reduction is realized for the motion of the pistons 22-24 by the fact that for a predetermined change of pressure in the respective actuator chamber 31-33 an increased piston stroke is required compared to the piston stroke when the inner diameter of the cylinders 19-21 is equal to the outer diameter of the pistons 22-24.

Each of the pistons 22-24 is moved by an actuator 25-27 which is symbolically represented as lever in the figures. For instance, electric step motors or magnetic coils can be used for the actuators.

Functioning—First Embodiment

Hereinafter the function of the zoom lens according to the first embodiment of the present invention is described in zoom operation.

If, for instance, in FIG. 3 the lens unit 3 is to be moved forward, the piston 22 is locked by the actuator 25, the actuator 26 is switched to idling so that the piston 23 can move freely and, the piston 21 is moved by the actuator 27 into the cylinder 21. In this way fluid provided in the actuator chamber 33 is forced into the fluid chamber 9 via the fluid conduit 18, whereby the lens unit 3 moves forward opposite to the spring force of the spring 11 and assisted by the spring force of the spring 12. By supplying fluid into the fluid chamber 9 the same quantity of fluid must be discharged from the fluid chamber 7 and/or 8. Since the piston 22 is locked, no fluid can be discharged from the fluid chamber 7 into the actuator chamber 31 via the fluid conduit 16. Thus fluid is equally forced out of the fluid chamber 8 into the actuator chamber 32 via the fluid conduit 17 as fluid is supplied to the fluid chamber 9. In this way the piston 23 is moved in the cylinder 20 in the outward direction. Moreover the spring 11 is compressed and the spring 12 expands.

In the foregoing the adjustment of the lens unit 3 was described in that the piston 22 is locked, the piston 23 remains freely movable and the piston 24 is moved into the cylinder. The same adjustment can be brought about, however, in that the piston 22 is locked, the piston 24 remains freely movable and the piston 23 is moved in the cylinder 20 in the outward direction. Moreover also two of the pistons 22-24 may remain freely movable and the third one of the pistons 22-24 can be moved into or out of the respective cylinder so as to simultaneously move both lens units 2 and 3.

In this way a plurality of possible combinations to drive the pistons 22-24 for obtaining the desired adjustment of the lens units 2 and 3 is resulting. Since these other possible combinations follow the same pattern as the one described above, a detailed description of all possible combinations is dispensed with.

In this way, in the present embodiment the lens units 2 and 3 can be appropriately moved by the actuators 25-27 to obtain a particular focal length. The actuators 25-27 are driven by a control (not shown) so as to obtain a quick and precise positioning of the lens units 2 and 3.

When driving the actuators 25-27 care has to be taken, however, that the control enables the amount of fluid supplied to the fluid chambers 7-9 to be equally discharged from the fluid chambers 7-9. That is to say, the control must not drive the pistons 22-24 in such a manner that, for instance, one of the pistons 22-24 is moved into the cylinder while the two other pistons 22-24 remain locked.

A strong curvature of the fluid conduits 16-18 can result in a pressure variation in the respective fluid conduits 16-18 and thus in the fluid chambers 7-9. This influence of the positioning of the lens units can be reduced, apart from the suitable arrangement of the fluid conduits 16-18 in the endoscope shaft (not shown), also by an appropriate adjustment of the spring forces of the springs 10-12. In this event, the springs 10-12 have to be adapted so that the elastic forces thereof are so strong that a lens unit 2 or 3 moves only from a predetermined pressure difference between two neighboring fluid chambers 7-9 which is higher than the pressure difference occurring when bending the endoscope shaft. In this way a more precise adjustment of the lens units 29 and 30 can be obtained which is not influenced by the curvature of the endoscope shaft.

Second Embodiment

Figure 5:
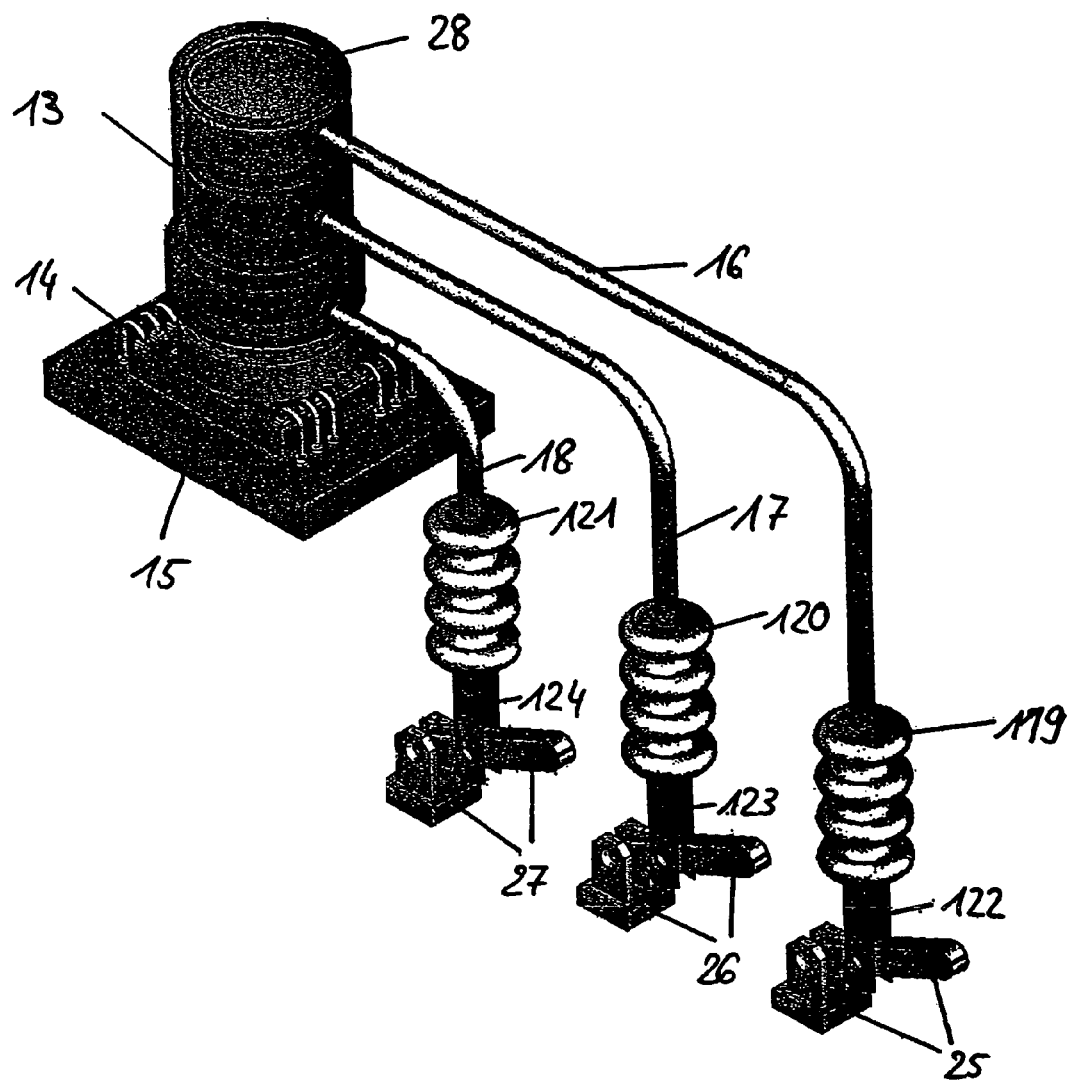
FIG. 5 is a spatial representation of a second embodiment of the zoom lens of the present invention.
Figure 6:
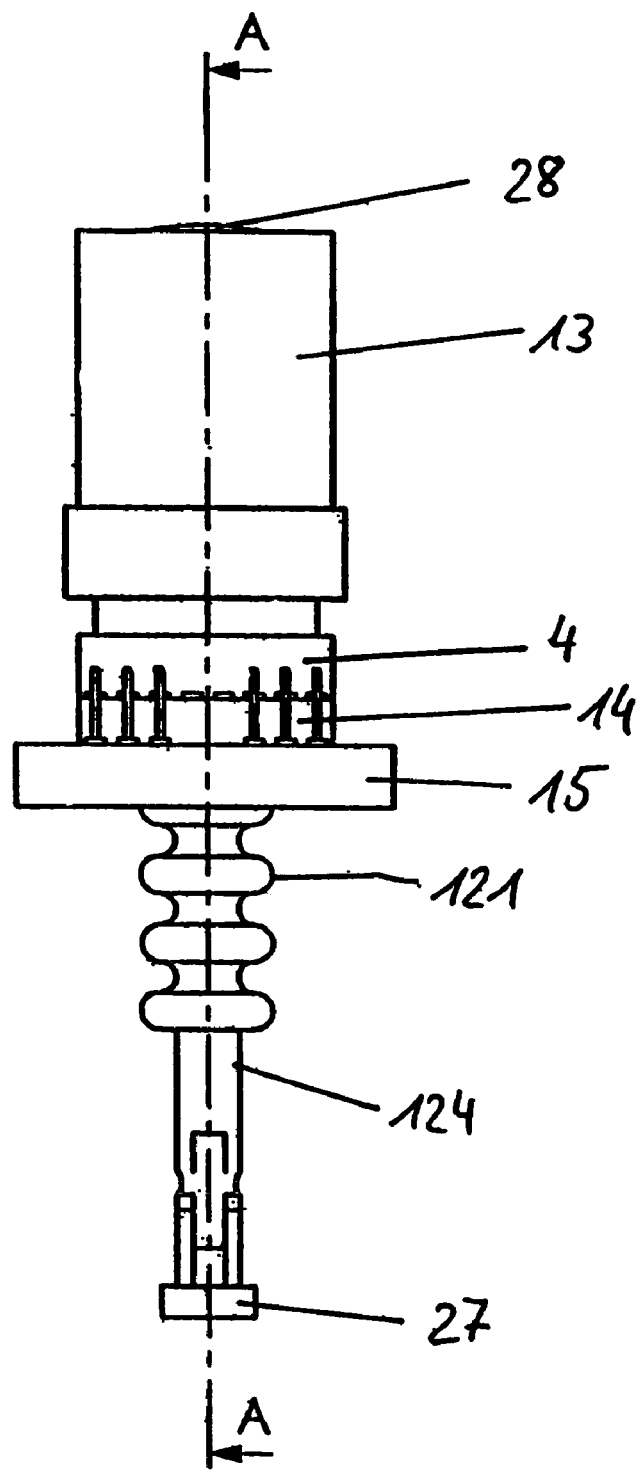
FIG. 6 is a side view of the zoom lens from FIG. 5.
Figure 7:
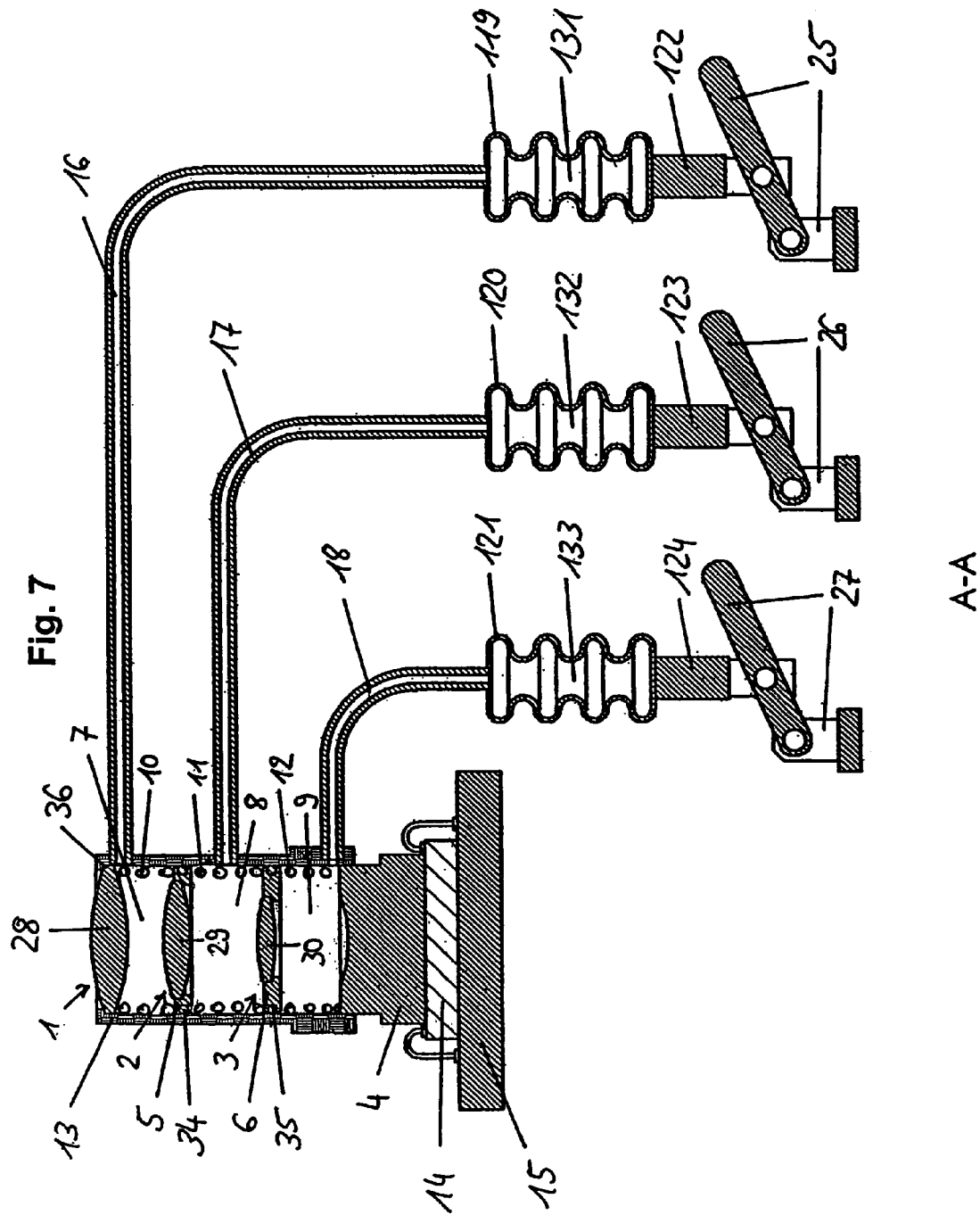
FIG. 7 is a sectional front view along the section A-A from FIG. 6.

By way of the FIGS. 5-7 the zoom lens for use in an endoscope shaft (not shown) according to a second embodiment is described in greater detail. The components in the FIGS. 5-7, which are identical with those from the FIGS. 1 to 3, have the same reference numerals and the description thereof is omitted hereinafter.

Now especially those components are described which differ from the first embodiment.

Instead of the cylinders 19-21 of the first embodiment, on the operating side of the fluid conduits 16-18 bellows 119-121 are connected to the fluid conduits 16-18. The interiors of the bellows 119-121 form actuator chambers 131-133 which are communicated with the corresponding fluid chambers 7-9 via the corresponding fluid conduits 16-18. At the side of the bellows 119-121 which is opposed to the fluid conduits 16-18 shafts 122-124 are connected to the outside of the bellows 119-121. These shafts 122-124 are connected, just as the pistons 22-24 of the first embodiment, with actuators 25-27.

When a shaft 122-124 in FIG. 7 is moved upwards, the pertinent bellows 119-121 are compressed and the volume of the corresponding actuator chamber 131-133 is reduced. Therefore fluid is forced out of the respective actuator chamber 131-133 via the pertinent fluid conduit 16-18 into the corresponding fluid chamber 7-9. When, vice versa, a shaft 122-124 in FIG. 7 is moved downwards, the pertinent bellows 119-121 are expanded and fluid is sucked from the pertinent fluid chamber 7-9. In this way, the same effect as by the piston-cylinder units of the first embodiment is achieved. For this reason a more accurate functioning of the second embodiment is not discussed, because, apart from the exchange of the piston-cylinder units for the bellows units, it is identical with that of the first embodiment.

First and Second Embodiments

When dimensioning the size of the actuator chambers 31-33 and 131-133 and arranging the fluid conduits 16-17, one of the lens units 2 or 3 has to be prevented from moving so far that one of the fluid chambers 7-9 is connected to a fluid conduit 16-17 which is provided for controlling another fluid chamber 7-9. That is to say, the fluid conduits 16-17 have to be connected with respect to the longitudinal direction of the lens cylinder 13 to the latter so that the lens units 2 and/or 3 can sufficiently move to and fro without, for instance during a forward motion of the lens unit 3, the fluid chamber being connected to the fluid conduit 17 and 18. For dimensioning the actuator chambers 31-33 and 131-133 this means that the volume thereof is selected to be only so big that, for instance during a forward motion of the lens unit 3, the fluid chamber 9 is not connected to the fluid conduit 17 and 18. As an alternative, this can also be prevented by appropriately fixed limits of the control which drives the actuators 25-27.

Third Embodiment

In a third embodiment the components which are identical with those of the first and second embodiment have equal reference numerals and the description thereof is omitted.

Figure 8:
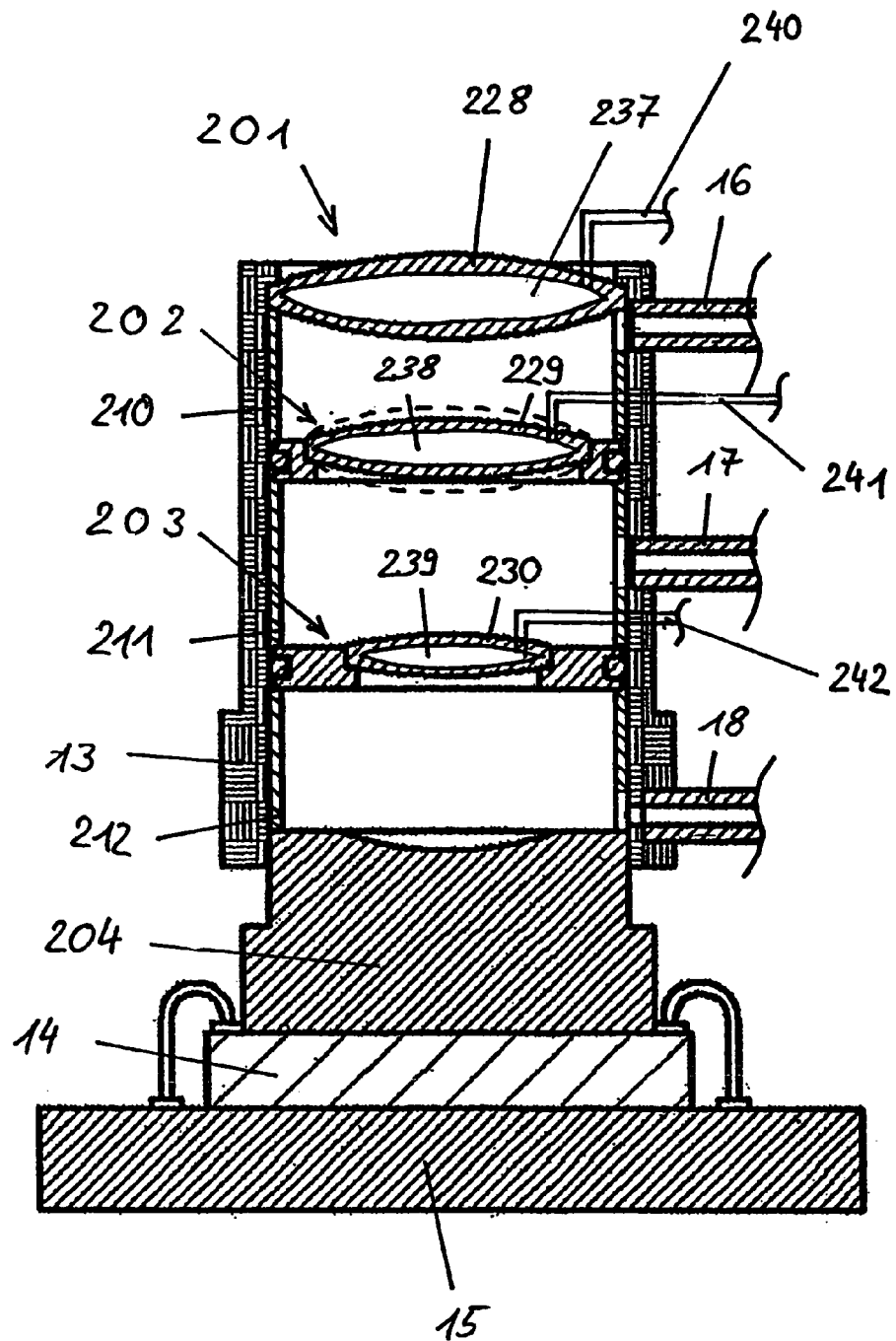
FIG. 8 is a front view of a third embodiment of the present invention sectioned across the center axis of the zoom lens.
Figure 9:
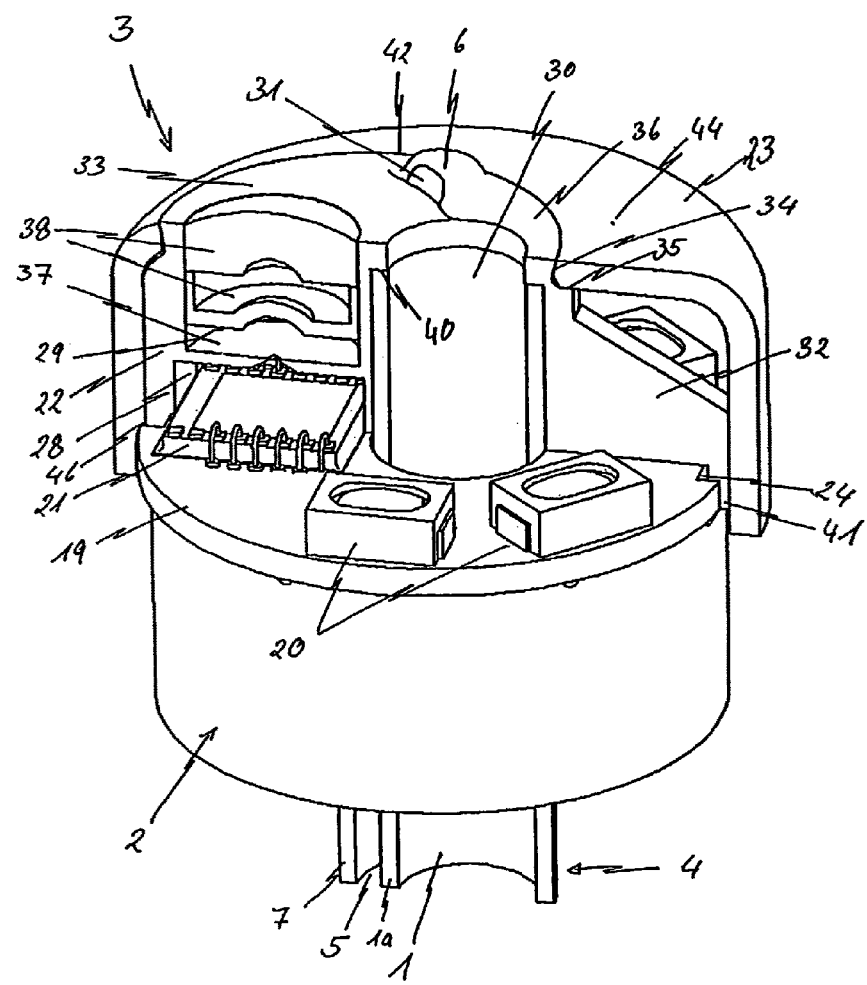
FIG. 9 is an endoscope head of an endoscopic device according to prior art.

By way of FIG. 8 the zoom lens for use in an endoscope head (not shown) according to a third embodiment is described in greater detail.

In the present embodiment, too, the lens cylinder 13 accommodates four lens units 201-204. The lens units 201-203 differ from the lens units 1-3 of the first and second embodiments by the fact that the lenses 228-230 are flexible lenses. These flexible lenses 228-230 are designed such that each of them forms a hollow or cavity 237-239 in the interior. The structure of the lenses 228-230 may be designed, for instance, so that two round bowl-shaped membranes are adjoined (e.g. glued) at their peripheries in such an airtight manner that the membranes arch outwardly in opposite directions and form a hollow 237-239 in the interior of each of the adjoined membranes. In the third embodiment the membranes adjoined in this way form the lenses 228-230 the hollows 237-239 of which are filled with a medium. Preferably a gas is provided as filling medium of the hollows, but also the use of an incompressible or easily compressible fluid is possible depending on the optical properties which are to be obtained. Moreover the hollows can be connected to hollow feeding tubes 240-242 which are shown schematically in FIG. 8. Via these hollow feeding tubes 240-242 the radii of curvature of the lenses 228-230 can be determined by supplying medium into the hollows or discharging medium from the hollows. To this end, for instance medium is supplied via the hollow feeding tubes 240-242 in order to reduce the radii of curvature of the membranes of the respective lenses 228-230 and/or to increase arching of the membranes of the lenses toward the outside, as schematically shown by a broken line in FIG. 8 for the lens 229. Accordingly, by discharging medium from the hollows 237-239 the radii of curvature of the membrane of the respective lenses 228-230 are increased and/or the membranes of the lenses are varied directed toward the inside. By this way of varying and/or adjusting the radii of curvature by means of the hollows 237-239 and the hollow feeding tubes 240-242 a possibility of varying the focal length of the individual lenses 228-230 was described which can be performed for each individual lens 228-230 independently of the other lenses 228-230. By varying the focal length of the individual lenses 228-230 likewise the total focal length of the zoom lens is variable, because the latter depends on the focal length of the individual lenses.

The lens unit 204 of the third embodiment is identical with the lens unit 4 of the first and second embodiments.

The above-described change of the pressure difference between the hollows 237-239 and the ambience or surroundings of the lenses 228-230, i.e. the fluid chambers 7-9, cannot only be realized by varying the pressure in the hollows 237-239, however, but also/in addition by a pressure variation in the fluid chambers 7-9.

For this purpose, the lens units 202, 203 in the third embodiment can be designed so that they are spaced apart in the axial direction of the lens cylinder 13 in a not displaceable manner. This fixing can be materialized, for instance, by a force fit of the lens units 202, 203 in the lens cylinder 13. In this embodiment, however, between each of the lens units 201-204 a sleeve 210-212 is arranged coaxially with respect to the lens cylinder 13. In this context, the outer diameter of the sleeves 210-212 is minimally smaller than the inner diameter of the lens cylinder 13. The sleeves 210-212 serve for arranging the lens units 202, 203 in the axial direction at a predetermined distance from each other and from the lens units 201, 204. In order to provide a communication of the fluid conduits 16-17 and the fluid chambers 7-9, at the positions where the fluid conduits 16-17 open into the fluid chambers 7-9 the sleeves 210-212 are provided with bores whose diameter is sufficiently large so that the inflow and outflow of fluid in and from the fluid chambers 7-9 is not hindered.

By supplying and discharging fluid to and from the fluid chambers 7-9 the radii of curvature of the membranes of the lenses 228-230 can equally be varied. For instance, by supplying fluid via the fluid conduit 17 to the fluid chamber 8 mainly the radii of curvature of the lenses 229 and 230 are varied. The possibility of adjusting the radius of curvature of the lenses by varying the pressure/volume of the fluid in the fluid chambers 7-9 can be combined with adjusting the radius of curvature by pressure/volume variation of the medium in the hollows 237-239 or they can be employed independently from each other. Moreover with the possibility of adjusting the curvature by means of pressure/volume variation of the fluid inn the fluid chambers 7-9 the hollow feeding tubes 240-242 can be dispensed with. In this case the hollows 237-239 would be filled with a fixed quantity of a compressible medium. This could apply pressure, for instance, to the hollows 237-239 in such a manner that it counteracts the fluid in the fluid chambers 7-9 so that the shape of the lenses 228-230 has a certain elasticity to maintain the shape.

The flexible lens 228-230 shown in this embodiment need not necessarily be combined with a fixed lens unit 202, 203, however, but can also be designed to have hydraulically adjustable lens units 2 and 3 which have been described in the first and second embodiments.

Accordingly, the fluid chambers 7-9 can be used for hydraulically displacing the lens units 2 and 3 in the axial direction of the lens cylinder, as described in the first and second embodiments, or can also be used for adjusting the radius of curvature of the membranes of the lenses 228-230.

Moreover it is also possible to realize the nondisplaceable axial spacing of the lens units 201-204 of the third embodiment by the fact that the fluid conduits 16-18, the sleeves 210-212 and the bores in the lens cylinder 13 for inserting the fluid conduits 16-18 are dispensed with. In the case of such a design, the fluid chambers 7-9 would be filled with a medium which is either incompressible or compressible and pressurized so that the lens units 202 and 203 are axially spaced apart at predetermined positions.

(Further Possibilities of Variation)

It is finally pointed out that the description provided here and the enclosed figures are only exemplary and are by no means intended to serve for restricting the invention to the configurations shown here. The invention permits a plurality of applications and modifications without leaving the core of the invention and the scope thereof.

Hereinafter some modifications will be mentioned:

In the first and second embodiments the hydraulic adjustment of the lens units (2, 3) was caused by the fact that fluid was supplied to and/or discharged from fluid chambers 7-9. This hydraulic adjustment of the lens units 2, 3 can also be caused by supplying or discharging fluid to or from fluid chambers formed by piston/cylinder units. More exactly speaking, this means that this fluid chamber is defined by the inner walls of a cylinder and the piston surface facing the interior of the cylinder of a piston inserted in the cylinder. The piston/cylinder units could be arranged in the wall of the lens cylinder 13 or in the ambience or surroundings of the wall of the lens cylinder 13. One active end of a piston/cylinder unit is functionally connected to a cylinder unit 2, 3 to be adjusted and the other active end of the piston/cylinder unit is connected either to another cylinder unit 2, 3 or to the lens cylinder 13. The functional connection of the one end of the piston/cylinder unit can be effected by the fact that this end is directly connected to a cylinder unit 2, 3 to be adjusted or, in the event that the piston/cylinder unit is arranged outside the lens cylinder 13, this end is effected by magnetic force or a connecting pin passing through the wall of the lens cylinder 13, wherein in the case of the latter possibility the opening required for the connecting pin would have to be sealed with a collar enclosing the connecting pin. The adjustable lens units 2, 3 are adjusted according to the same principle as in the case of the first and second embodiments, wherein the fluid chambers are correspondingly connected to the actuator chambers 31-33 via fluid conduits 16-18.

In the three embodiments the lens cylinder 13 is tubular, but it may also have different shapes, such as e.g. an elliptic shape. Then the lens units provided therein would have to be equally adapted to this modified geometry.

In the three present embodiments the invention was equipped with three lens units in each case, however the invention is not restricted to that and can be realized with a plurality of lens units.

In the described embodiments each lens unit includes one lens. This is exemplary, however, and a lens unit may include a plurality of convex or concave lenses.

The arrangement of springs 10-12 is not absolutely necessary. A configuration of the invention without springs is possible as well. Moreover the invention is not restricted to the use of spiral springs, as in the first and second embodiments, but it can also be realized with other springs.

In the described embodiments preferably an as incompressible fluid as possible was filled into the fluid chambers and a gas was filled into the hollows of the lenses. The invention is not to be restricted to that, however, but both gas and fluid can be used in the fluid chambers depending on the optical properties which the lens system of the zoom lens is to have.

The transmission of the visual information from the endoscope head to the operating end is not restricted, as described in the first and second embodiments, to the use of an optical sensor chip but can also be performed, e.g., with the aid of fiber optics.

Preferably the maximum dimension of the zoom lens in the longitudinal direction is 20 mm and the maximum diameter thereof is 10 mm.

The invention claimed is:

1. A zoom lens for endoscopic devices comprising:
   a lens mount;
   a plurality of lens units including a fixed first lens unit, a second lens unit and a fixed third lens unit arranged in the lens mount at an axial distance from each other, wherein the second lens unit is movable relative to the first lens unit and the third lens unit,
   a first fluid chamber formed in the lens mount between the first lens unit and the second lens unit;
   a first fluid conduit coupled to the first fluid chamber;
   a second fluid chamber formed in the lens mount between the second lens unit and the third lens unit; and
   a second fluid conduit coupled to the second fluid chamber,
   wherein a focal length of the zoom lens is hydraulically and/or pneumatically variable by varying an amount of fluid in one or more of the first fluid chamber or the second fluid chamber via one or more of the first fluid conduit or the second fluid conduit, and wherein the distance between the second lens unit and the first lens unit and the distance between the second lens unit and the third lens unit are hydraulically variable and/or the focal length of the lens units is pneumatically variable
   wherein a spring element is arranged in each of the first fluid chamber and the second fluid chamber between the plurality of lens units.

2. A zoom lens for endoscopic devices according to claim 1, wherein pressure chambers for hydraulically adjusting the focal length are formed in a wall of the lens mount or in an ambience of the wall.

3. A zoom lens for endoscopic devices according to claim 1, wherein each of the plurality of lens units includes at least one lens, and pressure chambers for hydraulically and/or pneumatically adjusting the focal length are formed between the lens units and/or inside of each respective lens.

4. A zoom lens for endoscopic devices according to claim 1, wherein at least one of the plurality of lens units further comprises a lens that forms a hollow and is formed of a flexible material so that a radius of curvature of the lens is variable by varying the pressure ratio between the hollow and an ambience of the lens.

5. A zoom lens for endoscopic devices according to claim 4, wherein a tube is connected to the hollow of the lens through which a medium can be supplied or discharged.

6. A zoom lens for endoscopic devices according to claim 5, wherein the variation of the pressure ratio for varying the radius of curvature of the lens is caused by supplying or discharging a fluid or gas through the tube.

7. A zoom lens for endoscopic devices according to claim 1, wherein a variation of a pressure difference for varying a radius of curvature of the lens is effected by supplying fluid to at least one of the first fluid chamber or the second fluid chamber and/or discharging fluid from at least one of the first fluid chamber or the second fluid chamber.

8. A zoom lens for endoscopic devices according to claim 1, wherein each of the fluid chambers is delimited by inner cylinder walls of a cylinder and a piston surface facing an interior of the cylinder of the piston which is inserted in the cylinder, one end of the piston/cylinder unit being functionally connected to one of the lens units and the other end of the piston/cylinder unit being fixed to a neighboring one of the lens units or to the lens mount.

9. A zoom lens for endoscopic devices according to claim 1, wherein hydraulic motion of at least one of the lens units is caused by supplying fluid to at least one of the first fluid chamber or the second fluid chamber and/or by discharging fluid from at least one of the first fluid chamber or the second fluid chamber.

10. A zoom lens for endoscopic devices according to claim 1, wherein a maximum dimension of the zoom lens in a longitudinal direction is 20 mm and a maximum diameter thereof is 10 mm.

11. A zoom lens preferably for endoscopic devices according to claim 1, wherein a sleeve is arranged between said respective lens units.

12. A zoom lens for endoscopic devices according to claim 1, further comprising an optical sensor chip for converting received optical information to electric signals.

13. A zoom lens for endoscopic devices according to claim 1, further comprising: a plurality of cylinders, a plurality of pistons each being movably arranged in the cylinders, wherein inner surfaces of the cylinders and outer surfaces of the pistons inserted in the cylinders form actuator chambers that are fluidly coupled to the fluid chambers through the plurality of the respective fluid conduits.

14. A zoom lens for endoscopic devices according to claim 13, wherein an outer diameter of the pistons is smaller than an inner diameter of the cylinders.

15. A zoom lens for endoscopic devices according to claim 13, wherein each piston is moved by a respective electric motor.

16. A zoom lens for endoscopic devices according to claim 15, further comprising a reduction unit arranged between each of the electric motors and the pistons.

17. A zoom lens for endoscopic devices according to claim 1, further comprising: a plurality of bellows having interiors that are fluidly coupled to the fluid chambers via the plurality of the respective fluid conduits; and a plurality of shafts, each of which is arranged at one end of the bellows to expand or compress the respective bellows by moving a shaft.

18. A zoom lens for endoscopic devices according to claim 17, wherein each of the shafts is moved by a respective electric motor.

19. A zoom lens for endoscopic devices according to claim 18, further comprising a reduction unit arranged between each of the electric motors and the shafts.

20. A zoom lens for endoscopic devices according to claim 1, wherein at least one of the lens units is fixed in a predetermined position by a medium provided in at least one of the fluid chambers.

21. A zoom lens for endoscopic devices according to claim 1, wherein at least one of the plurality of lens units further comprises at least one lens which further comprises two bowl-shaped parts.

22. A zoom lens for endoscopic devices according to claim 1, wherein at least two adjacent lens units are fluidly coupled to each other.

23. A zoom lens for endoscopic devices comprising:
a lens mount;
a plurality of lens units including a fixed first lens unit, a second lens unit and a fixed third lens unit arranged in the lens mount at an axial distance from each other, wherein the second lens unit is movable relative to the first lens unit and the third lens unit, wherein the second lens unit is hydraulically movable in an axial direction of the lens mount to vary the focal length of the zoom lens;
a first fluid chamber formed in the lens mount between the first lens unit and the second lens unit;
a first fluid conduit coupled to the first fluid chamber;
a second fluid chamber formed in the lens mount between the second lens unit and the third lens unit; and
a second fluid conduit coupled to the second fluid chamber, wherein a focal length of the zoom lens is hydraulically and/or pneumatically variable by varying an amount of fluid in one or more of the first fluid chamber or the second fluid chamber via one or more of the first fluid conduit or the second fluid conduit, and
wherein a spring element is arranged in each of the first fluid chamber and the second fluid chamber between the plurality of lens units.

24. A zoom lens for endoscopic devices comprising:
a lens mount;
a plurality of lens units including a first lens unit, a second lens unit, a third lens unit and a fourth lens unit arranged in the lens mount at an axial distance from each other,
a first fluid chamber formed in the lens mount between the first lens unit and the second lens unit;
a first fluid conduit coupled to the first fluid chamber;
a second fluid chamber formed in the lens mount between the second lens unit and the third lens unit;
a second fluid conduit coupled to the second fluid chamber;
a third fluid chamber formed in the lens mount between the third lens unit and the fourth lens unit; and
a third fluid conduit coupled to the third fluid chamber,
wherein the second lens unit and the third lens unit are axially moveable relative to the first lens unit and the fourth lens unit,
wherein the first lens unit and the fourth lens unit are axially fixed,
wherein a focal length of the zoom lens is hydraulically and/or pneumatically variable by varying an amount of fluid in one or more of the first fluid chamber, the second fluid chamber or the third fluid chamber via one or more of the first fluid conduit, the second fluid conduit or the third fluid conduit, and
wherein a spring element is arranged in each of the first fluid chamber, the second fluid chamber, and the third fluid chamber between the plurality of lens units.

25. A zoom lens according to claim 24, wherein the second lens unit and the third lens unit are fluidly coupled.

* * * * *